United States Patent [19]
Das et al.

[11] Patent Number: 5,817,473
[45] Date of Patent: Oct. 6, 1998

[54] METHOD AND DEVICE FOR IDENTIFYING A MYCOBACTERIUM SPECIES RESPONSIBLE FOR A MYCOBACTERIAL INFECTION

[75] Inventors: Pranab Khumar Das, Castricum; Remco Maria Van Es, Koog aan de Zaan; Hendrik Jan Houthoff, Amsterdam, all of Netherlands

[73] Assignee: Kreatech Biotechnology B.V., Ez Amsterdam, Netherlands

[21] Appl. No.: 454,122

[22] PCT Filed: Dec. 17, 1993

[86] PCT No.: PCT/NL93/00270

§ 371 Date: Nov. 20, 1995

§ 102(e) Date: Nov. 20, 1995

[87] PCT Pub. No.: WO94/14069

PCT Pub. Date: Jun. 23, 1994

[30] Foreign Application Priority Data

Dec. 17, 1992 [NL] Netherlands .......................... 9202197

[51] Int. Cl.$^6$ .................................................. G01N 33/53
[52] U.S. Cl. .................. 435/7.32; 424/163.1; 424/168.1; 424/248.1; 435/7.1; 435/172.3; 435/253.1
[58] Field of Search ...................... 435/2.1, 7.32, 435/172.3, 253.1; 424/92, 88, 8, 12, 168.1, 243.1, 163.1

[56] References Cited

U.S. PATENT DOCUMENTS 4,391,904 7/1983 Litman et al. .

OTHER PUBLICATIONS

Sada et al "An ElISA for the Serudiagnasis of Tuberculosis using a 30,000–Da Native Antigen of Mycobacterium tuberculosis" J. Infect. Des. 162:928–931, 1990.

Rambukkana, A. et al., "Subcellular Distribution of Monoclonal Antibody Defined Epitopes on Immunodominant Mycobacterium Tuberculosis Proteins in the 30–kDA Region: Indentification and 0Localization of 29/33–kDa Doublet Proteins on Mycobaterial Cell Wall". *Scandanvian Journal of Immunology*, vol. 33, No. 6, 1 Jun. 1991.

Vega–Lopez, F. et al., "Recognition of Mycobacterial Antigens by Sera from Patients with Leprosy." *Journal of Clinical Microbiology*, vol. 26, No. 12, 1 Dec. 1988.

Roche, P.W. et al., "Antibody Repsonses to the 18–kDa Protein of *Mycobacterium Leprae* in Leprosy and Tuberculosis Patients". *International Journal of Leprosy*, vol. 60, No. 2, 1 Jun. 1992.

Havlir, D.V. et al., "Human Immune Reponse to Mycobacterium Tuberculosis Antigens." *Infection and Immunity*, vol. 59, No. 2, 1 Feb 1991.

*Primary Examiner*—James C. Housel
*Assistant Examiner*—Rodney P. Swartz
*Attorney, Agent, or Firm*—Hoffmann & Baron, LLP

[57] ABSTRACT

A method for identifying a Mycobacterium species responsible for a mycobacterial infection in human or animal, comprising selecting a suitable mycobacterial species and strain; preparing at least one mycobacterial antigen, respectively antigen preparation; binding the antigen, respectively the antigen preparation to a suitable carrier, causing the binding antigen to react with antibodies from serum of an individual infected with a Mycobacterium species; making visible antigen-antibody reactions for a suitable antibody (sub-)class; and identifying the responsible Mycobacterium on the basis of the reactions which are made visible. The invention further provides a diagnostic kit which takes the form of a dip-stick on which is arranged a carrier strip with mycobacterial antigens binding thereto, and visualizing reagents antigen-antibody reactions occurring on the carrier after contact with the serum for testing. In another embodiment, the diagnostic kit comprises a micro titer plate, in the wells of which a specified antibody is arranged, and reagents for making visible antigen-antibody reactions occurring in the wells after contact with the serum for testing. The third embodiment is an immunoblot with mycobacterial antigens separated by electrophoresis binding thereto, and reagents for visualizing antigen-antibody reactions occurring on the immunoblot after contact with the serum for testing.

8 Claims, 4 Drawing Sheets

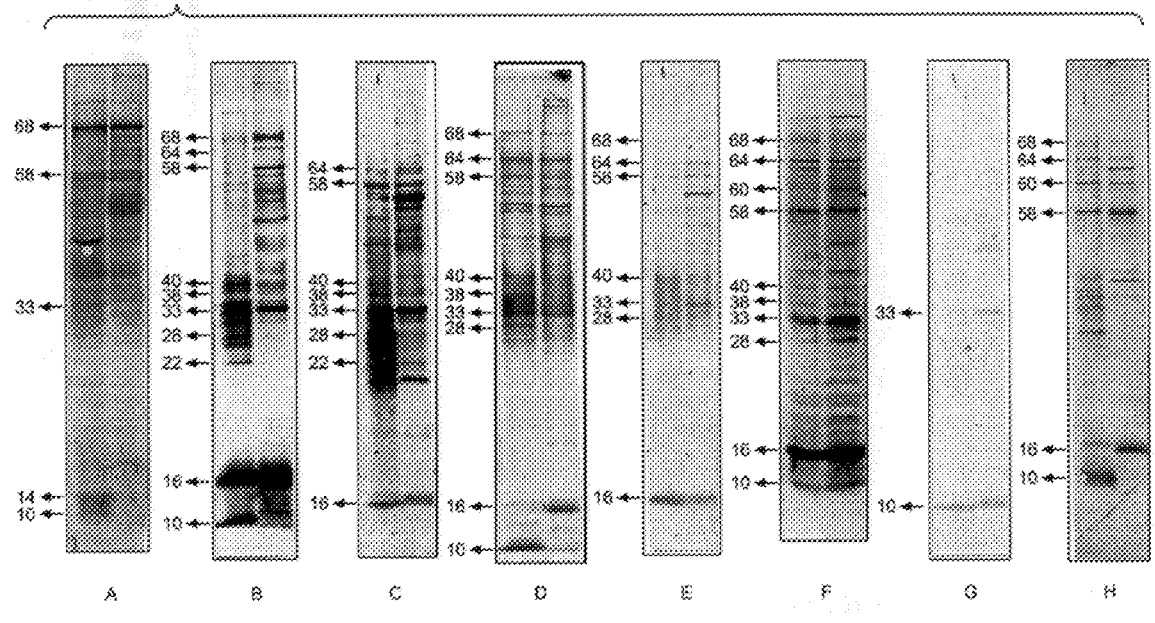

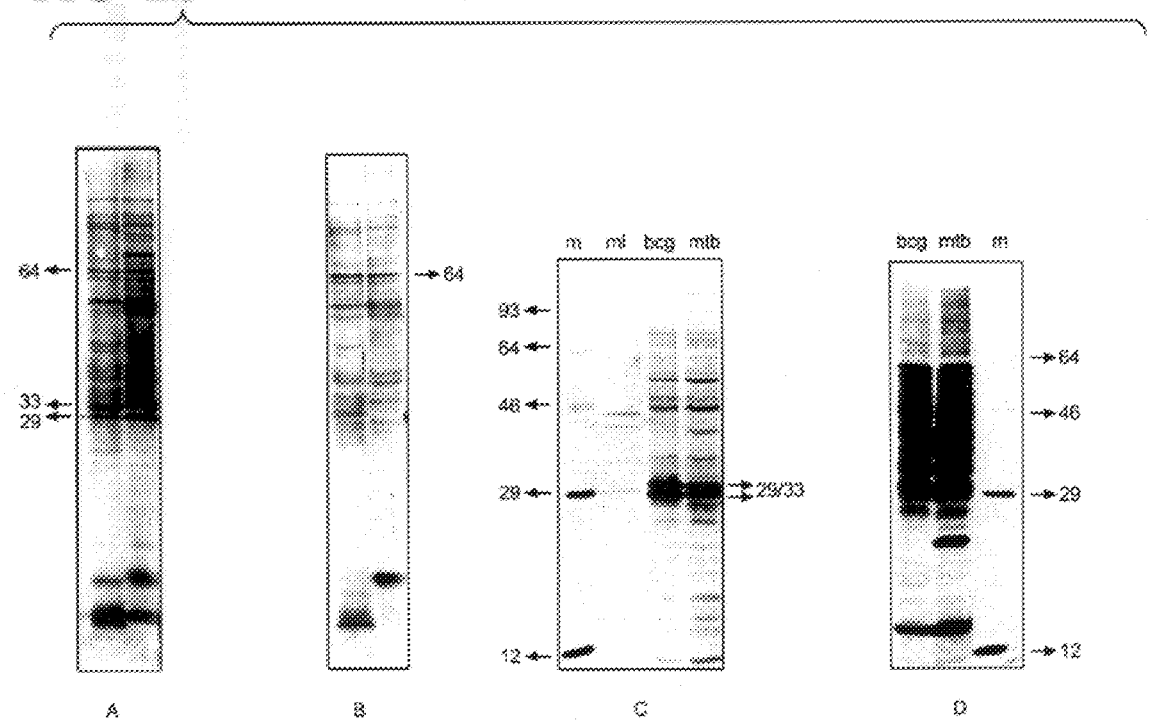

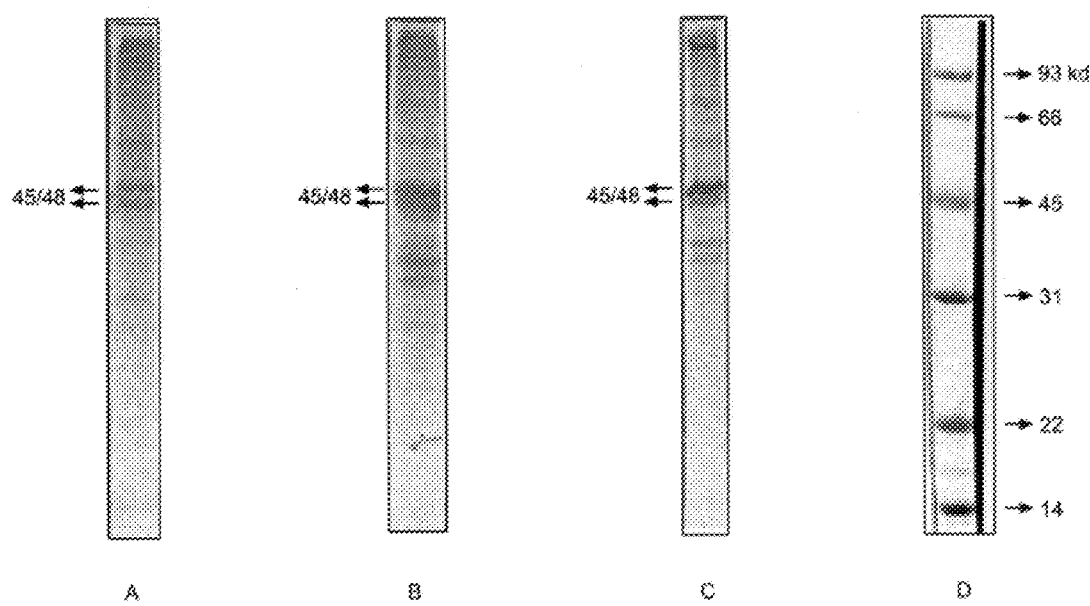

METHOD AND DEVICE FOR IDENTIFYING A MYCOBACTERIUM SPECIES RESPONSIBLE FOR A MYCOBACTERIAL INFECTION

The invention relates to a method for identifying a Mycobacterium species responsible for a mycobacterial infection in human or animal. The invention further relates to diagnostic kits for use in the method.

The genus Mycobacterium which contains about 50 species is responsible for a number of human and animal diseases which are known collectively as the mycobacterioses. The best known of these in humans is leprosy, caused by *M. leprae,* which affects more than ten million people worldwide, and tuberculosis, usually caused by *M. tuberculosis,* at least ten million new cases of which occur each year. Most other mycobacteria normally occur only as environmental saprophytes but can also cause opportunist diseases. This happens usually, but not only, in the case of people who have problems with their immune system, such as AIDS patients and people undergoing immunosuppression. These opportunist types comprise the slow-growing species *M. avium,* and the closely related *M. intracellulare* and *M. scrofulaceum* (often referred to together as MAIS complex), *M. kansasi, M. marinum* and *M. ulcerans,* and the fast-growing species *M. chelonae* and *M. fortuitum.* Although once rare, the incidence of opportunist mycobacterial diseases and tuberculosis shows a parallel increase in the western world with the incidence of AIDS. In addition there is limited but increasing evidence that mycobacteria or antigens thereof play a direct or indirect part in the etiology of a plurality of other diseases such as sarcoidosis and Crohn's disease and different auto-immune diseases such as auto-immune dermatitis, rheumatoid arthritis and diabetes. This could be attributed to a structural mimicry between epitopes of mycobacteria and those of the host.

The cell walls of mycobacteria are very complex and contain many lipids, some with structures unique to the genus. These structures comprise mycolinic acids and esters, peptido-glycolipide, arabino-galactane and lipo-arabino-manane. The lipid-rich mycobacterial cell walls are responsible for the characterizing colouring properties of the mycobacteria. They also enable mycobacteria to counter an attack by the immune system of the host. A number of species, once taken up into macrophages, are capable of surrounding themselves with a thick layer of secreted lipids.

Many different components of the mycobacteria begin an interaction with the immune system. These components comprise protein and hydrocarbon antigens, which can either be actively secreted by the mycobacteria or can form part of the cell wall or cell membrane. In addition they may be present in the cytoplasm, for instance in the cytoplasmic matrix, ribosomes and enzymes. Mycobacteria also possess immuno-modulating components such as immunosuppressing compounds and adjuvants. Consequently, a single mycobacterial species can induce a large variety of immune responses in different forms and with diverse specificities. It is therefore difficult to distinguish immune responses against species-specific components from cross reactions. For this reason it has therefore been found difficult to derive protein antigens suitable for the detection of species-specific humoral responses as a basis for a very sensitive and specific sero-diagnostic test for tuberculosis. Because the mycobacteria occur a great deal in the environment, human serum nearly always contains anti-mycobacterial antibodies.

In view of the problems with the specificity of protein antigens, a number of researchers, including the present inventors, have focused their attention on species-specific glycolipid antigens for the detection of specific humoral immune responses. Although the immune reactivity against mycobacteria is of the cell-mediated type and the humoral immune responses probably play a minor part in the total effector mechanism of mycobacterial immunity and immunopathology, studies into the antibody response to immuno-dominant mycobacterial cross-reactive antigen components (further referred to as Im-CRAC) could shed light on the varying capability of the host to recognize different mycobacterial antigens. They could therefore provide indirect information relating to the nature of the immune recognition of, and response to, a specific mycobacterial pathogen.

It has now been found that the clinical manifestation of mycobacterial diseases appears to be related to the varying capability of an individual host to produce a humoral response to different mycobacterial immuno-cross-reactive antigen components (Im-CRAC). Each mycobacterial infection generates its own specific antibody response to a number of specified antigens. Analysis of the antibody-response by means of immunoblotting has demonstrated that the immuno-dominant Im-CRAC vary in accordance with the immunopathological manifestation of the mycobacterial diseases. It has been found that the sera of individuals which are infected with different Mycobacterium species cause different and distinguishing band patterns on immunoblots of mycobacterial antigens.

BRIEF DESCRIPTION OF THE DRAWINGS

FIG. 2a shows an example of different Western blotting patterns developed after incubation with representative variable sera of tuberculous patients.

FIG. 2b shows an example of different Western blotting patterns developed after incubation with representative sera of patients with Lepromatous Leprosy (LL) and Tuberculous Leprosy (TT).

FIG. 2c shows an example of different Western blotting patterns developed after incubation with representative sera of patients with Crohn's Disease.

Figure 1:
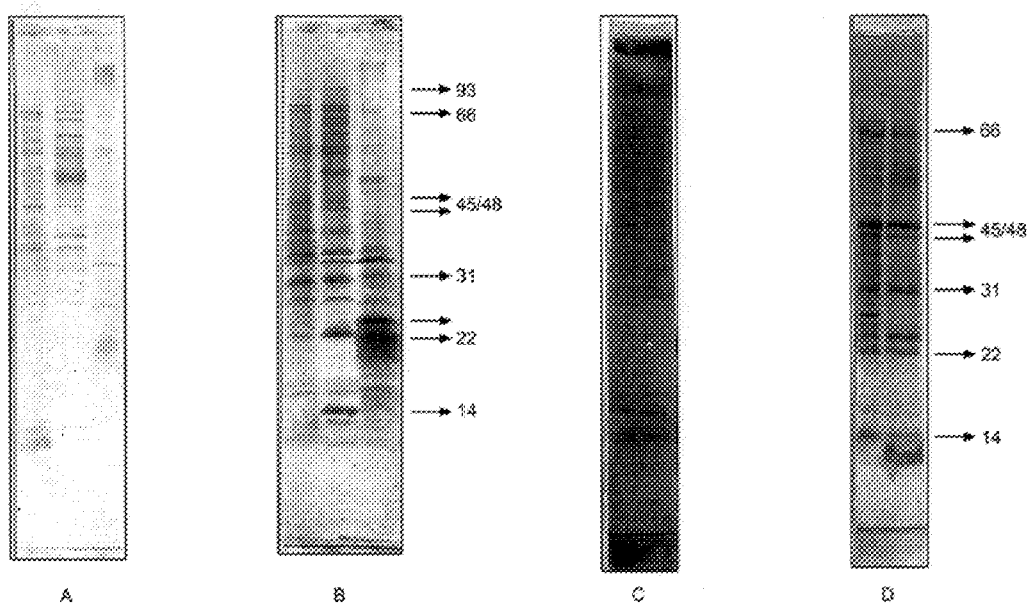
FIG. 1 shows an example of Western blotting patterns which are developed after incubation respectively with representative negative and positive sera (positive for bovine tuberculosis).

This discovery forms the basis of the present invention, whereby a method is provided for identifying a Mycobacterium species responsible for a mycobacterial infection in human or animal, comprising the steps of:

a) selecting a suitable mycobacterial species and strain;

b) preparing at least one mycobacterial antigen, respectively antigen preparation;

c) binding the antigen, respectively the antigen preparation to a suitable carrier;

d) causing the binding antigen to react with antibodies from serum of an individual infected with a Mycobacterium species;

e) making visible antigen-antibody reactions for a suitable antibody (sub-)class; and f) identifying the responsible *Mycobacterium* species on the basis of the reactions which are made visible.

In preference the antigen preparation is separated by electrophoresis prior to step c) and the carrier is a membrane to which the antigen is bound by means of electroblotting. This process is called Western blotting.

The Im-CRAC comprise namely a number of antigens with specific molecular weights which, as has now been found, after immunoblotting exhibit a binding pattern which correlates to the disease, respectively infection. The specific band pattern is characterized by the presence or absence of four individual components, for instance:

a region comprising different pronounced bands and/or overlapping bands, which can be observed as a smear ("region");

sharp single bands which are strongly positive ("band");

sharp double bands which are strongly positive ("doublet"); and other positive bands ("extra bands").

For a survey of the different antigens, their molecular weights and binding characteristics, see table 1.

TABLE 1

Survey of characteristic binding patterns of mycobacterial Immuno-Cross-reactive Antigen Components.

| Antigen | Diagnostic for | MW range (in KDa) | Binding characteristic |
|---|---|---|---|
| A | J | <8 | band |
| B | T, B, J, | 10–16 | band |
| C | B, J, T, | 20–28 | band or region |
| D | L | 29/33 | doublet |
| E | B, J, T, | 31–40 | band or region |
| F | T | 38–40 | band or region |
| G | C, B, J, | 45/48 | doublet |
| H | T | 58–60 | band or region |
| I | L | 64/65 | doublet |
| J | J | 66 | band |
| K | T | 68 | band |
| L | L | 30–64 | region |

T: Human Tuberculosis
L: Leprosy
C: Crohn's Disease
B: Bovine Tuberculosis
J: Johne's Disease The mycobacterioses are all characterized by a specific banding pattern which is formed when a blot having thereon an antigen preparation of mycobacteria separated to size is incubated with serum of an infected individual.

The tables 2a–2e below show a survey of the banding patterns of a number of mycobacterial, respectively immunological diseases.

TABLE 2a

Bovine tuberculosis Regions (MW in KDa)

| Pattern | and/or 10–16 | and/or 20–28 | and/or 31–40 | and 45–48 |
|---|---|---|---|---|
| 1. | 14 KDa band | 22 KDa band 20–28 KDa region | 31 KDa band | 45/48 KDa doublet |

Johne's Disease Regions (MW in KDa)

| Pattern | and/or >8 | and 10–16 | and/or 20–28 | and/or 31–40 | and 45–48 | and 66 |
|---|---|---|---|---|---|---|
| 1. | region | 14 KDa band | and 22 (25) - KDa band, and/or 27 KDa band | 31 KDa band | 45/48 KDa doublet | 66 KDa band |

TABLE 2b

Human Tuberculosis Regions (MW in KDa)

| Pattern | 10–16 | 20–28 | 31–38 | 38–40 | 58–60 | 68 | other* |
|---|---|---|---|---|---|---|---|
| 1. | 10 and 16 KDa bands | / | 33 KDa band | region | bands | / | +/– |
| 2. | 16 KDa single band | region | 33 KDa band | bands | region | / | +/– |
| 3. | 10 or 16 KDa band | / | / | bands | bands | / | +/– |
| 4. | 16 KDa band | / | 33 KDa band | region | bands | / | +/– |
| 5. | 10 and/or 16 KDa band | region | 33 KDa band | bands | bands and/or region | 68 KDa band | +/– |

*Extra bands and/or regions can colour but are not diagnostic for Human Tuberculosis TABLE 2c Leprosy Regions (MW in KDa)

| Pattern | 29–33 | 30–65 | 64–65 | other* |
|---|---|---|---|---|
| LL pattern 1 | 29/33 KDa doublet | / | / | +/– |
| TT pattern 1 | / | regions and/or bands | / | +/– |
| TT pattern 2 | / | regions and/or bands | 64/65 KDa doublet | +/– |
| TT pattern 3 | / | / | 64/65 KDa doublet | +/– |

*Extra bands and/or regions can colour but are not diagnostic for leprosy

TABLE 2d

Crohn's Disease Regions (MW in KDa)

| Pattern | 45-48 | other* |
|---|---|---|
| 1. | 45/48 KDa doublet | +/– |

*Extra bands and/or regions can colour but are not diagnostic for Crohn's Disease TABLE 2e Rheumatoid Arthritis Regions (MW in KDa)

| Pattern | and 42 KDa | and/or 80–90 KDa | and/or 58–60 KDa | and/or 14–18 KDa |
|---|---|---|---|---|
| 1. | band | region | region | region |

When an immunoblot is used, two questions can be answered. Firstly, the presence of any positive band pattern will answer the question of whether a mycobacterial infection is present. Secondly, the presence of specific banding patterns indicates which mycobacterial species has caused the infection, and therefore what the nature and etiology of the disease will be.

The invention further relates to a heterogeneous enzyme immunoassay.

From the patterns in the immunoblotting it follows which mycobacterial antigens respectively antigen preparations are suitable for diagnosis of any particular disease.

The antigen for a heterogeneous enzyme immunoassay is preferably chosen from the group which consists of mycobacterial immuno-cross-reactive antigen components with a molecular weight of 29/33 KDa, 45/48 KDA, and 64/65 Kda and a fraction designated with the term KP-100. These ImCRAC can be used separately or in combination with each other for serological diagnosis of the correlating diseases in a heterogeneous enzyme immunoassay (EIA).

In this form of assay antibody-conjugates labelled with a standard enzyme are used. An important detail is that the enzyme activity does not change during the immunological reaction.

In order to test the immune response in patients to the selected antigens, use is made for instance of microtiter plates ("Solid Phase"). By means of standard published techniques the antigens are irreversibly immobilized on the surface of the wells in such a microtiter plate.

This binding takes place while retaining specific antigen determinants on the used antigens. After incubation with serum, in the wells of the microtiter plate, antibodies present therein can specifically form a complex with the irreversibly bound antigens.

After removal of non-binding serum components, binding antibodies are detected using an anti-antibody antibody labelled with an enzyme.

Binding of the enzyme is only possible when specific antibodies have adhered to the immobilized antigens. Substrate conversion by the binding enzyme to a visually or photometrically observable signal is thereby directly related to the presence of specific antibodies in the tested serum.

The choice of specificity of the enzyme-bound anti-antibody antibody determines the type of reaction that takes place. For instance, it may be desirable in some cases to demonstrate the specifically binding immunoglobulins of the IgG type, while in other cases immunoglobulins of the IgA and/or IgM type are just demonstrated.

The combination of antigen and immunoglobulin type defines the specificity of the test.

The said methods, that is, the immunoblot and the EIA, can be used as mutual confirmation.

In addition, for the serological diagnosis based on the said antigens, use can be made of a test stick as solid phase.

A particularly advantageous embodiment of the invention relates to a test stick, the so-called "dip-stick", which is used as solid phase in the heterogeneous enzyme immunoassay.

The said mycobacterial antigens can be irreversibly bound to such a dip-stick.

The antigen is brought into reaction with antibody from serum for testing by dipping the dip-stick in a serum sample for testing. The formed antigen-antibody complex can be made visible by subsequently dipping the dip-stick in an anti-antibody antibody-enzyme conjugate solution.

With the binding enzyme a substrate can then be converted to a visually or photometrically observable signal.

The invention provides a diagnostic kit for:
- an immunoblot assay; comprising ImCRAC antigens separated by electrophoresis as described above, immobilized on a solid carrier, in addition to an associated suitable detection system.
- a heterogeneous enzyme immunological assay; comprising a microtiter plate, the wells of which are coated with above mentioned antigens or antigen preparations, in addition to an associated suitable detection system.
- a dip-stick assay; comprising test sticks coated with antigen or antigen preparations, in addition to an associated suitable detection system.

The present invention will be further elucidated with reference to a number of examples which are given herein by way of illustration and are not intended to limit the invention.

EXAMPLE 1

Immunoblot

1. Preparation of Crude Mycobacterial Mass ("Starting Material")

The mycobacteria were cultured in commercially available Sauton medium supplemented with 2 g $MgSO_4$, 8 g citric acid, 2 g $K_2HPO_4$, 16 g asparagine, 2 g ($Fe^+$) ammonium citrate, 240 ml glycerol. The bacteria were cultured under standard conditions. The cells were harvested by filtration of the culture medium with a 12 $\mu$m filter. The cells were subsequently resuspended in 20 ml PBS (phosphate-buffered salt solution) (pH 7.4) and the harvested cells were autoclaved under a pressure of 15 Psi for 20 minutes in order to deactivate and sterilize the bacteria. The thus obtained bacterial mass can be stored at −80° C.

In order to determine the quantity of starting material a 1/100 dilution of the harvested autoclaved suspension in PBS was made. The optical density thereof, measured at 420 nm ($O.D._{420}$) must be 0.1. If necessary the concentrated bacterial mass is supplemented with PBS (pH 7.4) until the correct O.D. is obtained. An $O.D._{420}$ of 0.1 indicates the presence of $7 \times 10^{11}$ bacteria per 30 ml, which is equivalent to 12 g wet weight of the bacterial mass.

For preparation of a crude mycobacterial extract 5 g wet weight of the bacterial mass was washed three times with PBS (pH 7.4). Centrifuging was then carried out at 3000×g until the mass precipitated. The pellet was suspended in 50 ml PBS and stirred carefully to reduce formation of lumps to a minimum. To prevent lump forming 0.05% Tween 80 was optionally added. In order to avoid bacterial contamination 3 mg penicillin/streptomycin was added to this solution. The concentration was then brought with PBS to 2 g wet weight/ml.

The bacterial mass was subsequently broken open using an automatic French-X-press or RIBI press (American Instruments Company, Trevenollab. Inc. Maryland). The buckets were pre-cooled overnight at −20° C. Before use the buckets were held in a mixture of ethanol and dry ice (−20° C.). After the buckets were filled with 1 g bacterial mass per bucket of 5 ml and cooled at −80° C. for 20 minutes, the buckets were placed in the French-X-press and 12 tons of pressure were applied by pushing in the plunger of the press. The buckets were then removed and cooled again at −80° C. for 20 minutes. The buckets were inverted and treated for the second time. 10 tons of pressure were applied the second time. Cooling and breaking were then repeated a number of times, normally about 5 times. The disrupted cells were eluted with a suitable volume of PBS and subsequently centrifuged at 4° C. at 300×g for 10 minutes in order to remove the unbroken bacteria with the sediment. The collected supernatant was then centrifuged at 4° C. and 145,000×g for 2 hours. The pellet was suspended in 0.1M Tris-HCl (pH 7.2), 0.01M EDTA which contained 20 mM $MgSO_4.7H_2O$ in a concentration of about 1 g per 10 ml. 1 mg RNase and 1 mg DNase were added per 10 ml volume. Incubation then took place overnight at 4° C. with careful stirring. Incubation thereafter took place for 1 hour at 37° C.

and the lysate was centrifuged at 300×g and 4° C. for 10 minutes in order to remove the last-remaining unbroken bacteria (this is further referred to as "starting material").

2. Manufacture of Membrane for Assays

A 12% polyacrylamide analytical gel of 1.5 mm thickness was manufactured according to normal standard procedures. No comb was used in the stacking gel. 5 mg of the starting material obtained under 1. (100 mg per ml), respectively KP-100 or SP-100 (see example 2) were used for each gel. 40 microliters of this material was diluted with 1200 microliters PBS. 300 microliters 5× loading mixture (0.3 g 250 mM Tris-HCl, 1.0 g 10% SDS, 1.0 g 10% dithioerytreitol, 5 mg 0.05% bromophenol blue) was then added.

Incubation was carried out for 20 minutes at 65° C. 1500 microliters were subsequently applied to the gel and electrophoresis performed under the following conditions: 150 V for the run through the stacking gel for 30 minutes and 100 V through the running gel for 6 hours.

In order to form a Western blot the proteins present in the gel were transferred at 50 V for 3 hours to a nitrocellulose membrane. After completion of the transfer the membrane was coloured with 1.5% amido black for 2 minutes to check the membrane for irregularities and air bubbles. The membrane was then decolourized in 0.05% Tween 80 in PBS with 1% BSA (bovine serum albumin). The membrane was then cut into strips and was ready for use.

3. Immunodetection

The strips were incubated with 1:200 diluted human serum. The serum was diluted in PBS with 3% BSA. The incubation took place for 1 hour at room temperature. The strips were subsequently washed three times (for 3 minutes at a time) in PBS. The strips were then incubated with a goat anti-total-human immunoglobulin-alkaline phosphatase conjugate in a dilution of 1 to 1000 in PBS with 3% BSA and 0.05% Tween 80. Washing in PBS then took place again three times. The colour was developed with an NBT/BCIP (nitroblue tetrazolium/Bromo, Chloro Indolyl phosphate) colour solution (1 mg per 10 ml) to which 10 microliters $H_2O_2$ were added. The strips were incubated for a maximum of 2 hours in 1 ml of this solution per strip. The colour reaction was stopped by transferring the strips to 0.1M Tris-HCl (pH 8.3), 0.01M EDTA. The obtained patterns are interpreted by comparison with a reference pattern.

The results are shown in FIGS. 1 and 2a–2c.

FIG. 1 shows in the blots A and B an example of Western blotting patterns which are developed after incubation respectively with representative negative and positive sera (positive for bovine tuberculosis).

Blots C and D are an example of Western blotting patterns which are developed after incubation with a representative negative and positive serum sample, respectively (positive for Cattle Jones Disease).

Blots A and B: Lane 1: BCG crude extract, Lane 2: crude extract of an M. tuberculosis strain, Lane 3: Myc. bovis crude extract.

Blots C and D: Lane 1: BCG derived KP-100, Lane 2: RIVM 7114 derived KP-100. RIVM is the abbreviation for the Netherlands National Institute of Public Health and Environmental Protection (Rijksinstituut voor Volksgezondheid en Milieuhygiene, Bilthoven, the Netherlands).

Interpretation of banding patterns from left to right is as follows.

Only the specific characteristics are stated herein.

Blot A: only the background bands can be observed in blots incubated with negative serum.

Blot B: region in the 10–16 KDa region in lane 3, 22 KDa band in lane 2, 31 KDa bands in lane 1 and 2, 14 KDa band in lane 2.

Blot C: only background bands can be observed in blots incubated with negative serum.

Blot D: 45/48 KDa doublet in lane 1 and 2, 22 and 25 KDa band in lane 1 and 2, 66 KDa band in lane 1 and 2, 27 KDa band in lane 1.

FIG. 2a is an example of different Western blotting patterns developed after incubation with representative variable sera of tuberculosis patients. Noticeable is the combination of different patterns demonstrating the presence of different dominant bands, as shown in table 1. These band patterns function as "hallmarks" for TB patients as diagnosed serologically.

Applicable to all blots (from left to right): Lane 1=BCG crude extract, Lane 2=crude extract of an M. tuberculosis strain.

Interpretation of banding patterns is as follows. Different blots (originating from different PAGE gels) are herein compared with each other.

Blot A: Mycobacterium avium infected patient.

Blot B–F: Tuberculosis patients.

Blot G: non-endemic negative serum.

Blot H: endemic negative serum (known recent contact, blot developed 2 weeks after patient returned to Netherlands from endemic range).

Only "hallmarks" are mentioned.

Blot A: Mycobacterium avium infected patients, sera, band at 68 KDa in lane 1 and 2, range in 10–16 KDa in lane 1, band in the 58–60 KDa region in lane 2. Patient shows low IgA titer in P-90 ELISA).

Blot B: 38–40 KDa band in lane 1 and 2, 10–16 KDa band in lane 1 and 2, band in 58–60 KDa region in lane 2, smear in 22–28 KDa region in lane 1.

Blot C: 16 KDa band in lane 1 and 2, bands in 58–60* KDa region in lane 1 and 2, bands in 38–40 KDa region in lane 1 and 2, smear in 22–28 KDa region in lane 1, 33 KDa band in lane 1 and 2.

Blot D: 10 KDa band in 10–16 KDa region in lane 1, 16 KDa band in 10–16 KDa region in lane 2, 68 KDa band in lane 1 and 2, bands in 58–60* KDa region in lane 1 and 2.

Blot E: smear in 33–38 KDa region in lane 1 and 2, 16 KDa bands in lane 1 and 2, bands in 58–60* KDa region in lane 2.

Blot F: bands in 10–16, 22–28, 38–40, 58–60 regions and 68 KDa band in both lanes 1 and 2.

Blot G: non-endemic negative serum.

Blot H: endemic negative serum (known contact).

FIG. 2b is an example of different Western blotting patterns developed after incubation with representative sera of patients with Lepromatous Leprosy (LL), Blot A and C, and Tuberculous Leprosy (TT), Blot B and D.

The "hallmark" patterns are shown in table 1 and are for LL: distinctive 29/33 KDa doublet, and for TT: distinctive 64/65 KDa doublet (often observed as single band) or a very pronounced smear in the 30–64 KDa region.

To Blot A and B are applied: Lane 1: BCG crude extract, Lane 2: crude extract of a M. tuberculosis strain, Blot C: Lane 1: Molecular marker, Lane 2: not relevant, Lane 3: BCG crude extract, Lane 4: crude extract of an M. tuberculosis strain, Blot D: Lane 1: BCG crude extract, Lane 2: crude extract of an M. tuberculosis strain, Lane 3: Molecular marker.

Interpretation of banding patterns, wherein only the "hallmarks" are mentioned, is as follows:

Blot A/C: 29/33 KDa doublet in lane 1 and 2.

Blot B/D: 64/65 KDa doublet in lane 1 and 2.

Noticeable is the very intensive smear in the 30–64 KDa range on blot D.

Finally, FIG. 2c is an example of different Western blotting patterns developed after incubation with representative sera of patients with Crohn's Disease. The "hallmark" patterns are shown in table 3 and are for Crohn's Disease a pronounced 45/48 KDa doublet.

Applied to blot A is: BCG crude extract, blot B: crude extract of an *M. tuberculosis* strain, blot C: *Mycobacterium avium* crude extract, blot D: molecular marker.

Interpretation of banding patterns is as follows:

All lanes show a distinctive colouring of the 45/48 KDa doublet positivity, which indicates Crohn's Disease. The 45/48 KDa doublet reacts positively in 65% of all Crohn patients.

EXAMPLE 2

Enzyme Immunoassay

1. Preparation of Antigens

The starting material (see EXAMPLE 1 under 1.) was, depending on the chosen *M. tuberculosis* strain, centrifuged at 70,000×g to 120,000×g at 4° C. for 2 hours. The pellet was washed three times with PBS. Between the washing steps centrifuging took place at 70,000×g to 120,000×g at 4° C. for 2 hours. The pellet was collected and resuspended in 10 ml PBS. In addition to the supernatant in Example 1, SP-100 can also be used for immunoblots (example 1) and enzyme immunoassays (this example). The suspension was subsequently sonified for 2 minutes at 80 watts at 4° C. After the protein concentration was determined, quantities of 100 μl were frozen at a concentration of 1 mg/ml and stored at –80° C. until time of use (this preparation is designated with the term KP-100).

30 mg of the starting material was then applied in the presence of loading mixture onto a preparatory 12% polyacrylamide gel of 0.5 cm thickness after 20 minutes of incubation at 65° C. Electrophoresis was carried out for 30 minutes at 150 V (stacking gel) and for 6 hours at 100 V (running gel). The electrophoresis was stopped after the blue colorant band had disappeared from the gel. The gel was then cut into horizontal strips of 2 mm thickness which in turn were divided into pieces of 1 cm length. The gel pieces were each eluted overnight at 4° C. in a tube with 5 ml sterile distilled water. Thorough mixing thereafter took place and the remaining gel pieces were centrifuged to the bottom.

The elution was checked using a 12% polyacrylamide analytical gel of 1.5 mm thickness. The gel was cast with a comb. After 20 minutes incubation at 65° C. 40 μl of each tube with gel pieces was placed in the slots in the presence of 10 μl 5× loading mixture. The electrophoresis was carried out for 30 minutes at 150 V in the "stacking gel" and for 6 hours at 100 V in the "running gel". The electrophoresis was stopped and the gel made ready for preparation of a Western blot. The blotting procedure is described in EXAMPLE 1 under 2. Similar results were obtained using HPLC, FPLC and other routine separating procedures.

In order to establish which fractions contain the relevant antigens, strips of the blot were incubated with sera of patients with lepromatous leprosy, tuberculous leprosy and Crohn's Disease. Shown herewith are respectively the 29/33 KDa antigens, the 64/65 KDa antigen and the 45/48 KDa antigens. The complex formation was visualized using anti-human IgG peroxidase conjugate and DAB. The desired fractions were collected, combined and used to coat a microtiter plate (see below).

2. EIA

Microtiter plates are coated (via standard techniques) with either KP-100, SP-100, starting material, whole bacteria, 29/33 KDa, 64/65 KDa or 45/48 KDa antigens.

After coating the plates are blocked, in order to prevent an aspecific binding of serum components, with a 3% bovine serum albumin (BSA) solution. Plates are then dried and stored at 4° C.

2.1. Tuberculosis EIA Test (Microtiter Plates Coated with KP-100)

Test sera are pipetted in a 1:100 dilution into the coated wells of a microtiter plate. The reaction takes place for 1 hour at 37° C. Aspecific serum components and non-binding serum components are washed away in a washing step. A second incubation with a suitable dilution of an anti-human IgA peroxidase conjugate is carried out again for 1 hour at 37° C., and excess conjugate is then washed away.

Indication of human antibodies of the sub-type IgA binding specifically to KP-100 takes place by adding TMB (tetramethylbenzidine) to the wells.

Binding enzyme results in the occurrence of a blue colour which, after addition of a colouring stop solution, changes to yellow. This yellow colour has an absorption maximum of 450 nm.

The intensity of the resulting colour is proportional to the amount of bound KP-100-specific IgA.

The results are shown in the tables below.

In the described test patient and control sera are used from two different populations.

A=Endemic area (Africa, Ghana)

B=Non-endemic area (Europe, the Netherlands).

Each population is sub-divided into 4 sub-groups, namely:

Group 1=culture confirmed TB patients

Group 2=negative control group (normal healthy individuals

Group 3=suspected positives (TB contacts)

Group 4=suspected negatives (no known data, but certainly no TB, possibly leprosy or other aspecific Mycobacteriosis).

The test is performed with two kits having different lot numbers and production dates.

Interpretation of the test results takes place on the basis of the so-called calibration line which is made up of control sera with a determined arbitrary unit definition which corresponds to a known OD value (1 unit, 4 units and 8 units).

Each time a test is carried out the units are included in the assay. Found sample values can then be related to the unit definition.

A test serum can be considered positive when the result found in the test scores higher than 2.1 units.

A test serum can be considered negative when the result found scores lower than 1.2 units.

Test sera with unit values between 2.1 and 1.2 units fall into the set so-called reconfirmation zone. This means that in the first instance positivity or negativity for tuberculosis cannot be determined with this test.

Reconfirmation of these sera takes place using the described Western blot strips with which, after serum incubation on the basis of banding patterns and specific "hallmarks", an answer can be given to the question of whether the test serum is positive (bands present) or negative (bands absent).

TABLE 3

Population A. Endemic range:
Group 1:

| SERUM NO. | # UNITS | TEST SCORE | REMARKS |
| --- | --- | --- | --- |
| 1 | 2.44 | positive | culture positive |
| 2 | 3.43 | positive | culture positive |
| 3 | 1.78 | reconfirmation | culture positive |
| 4 | 1.37 | reconfirmation | culture positive |
| 5 | 5.74 | positive | culture positive |
| 6 | 3.21 | positive | culture positive |
| 7 | 1.66 | reconfirmation | culture positive |
| 8 | 2.00 | reconfirmation | culture positive |
| 9 | 2.00 | reconfirmation | culture positive |

TABLE 4

Population A. Group 2:

| SERUM NO. | # UNITS | TEST SCORE | REMARKS |
| --- | --- | --- | --- |
| 10 | 1.16 | negative | healthy individual |
| 11 | 0,86 | negative | healthy individual |
| 12 | 0.77 | negative | healthy individual |
| 13 | 0.64 | negative | healthy individual |
| 14 | 0.74 | negative | healthy individual |
| 15 | 0.79 | negative | healthy individual |

TABLE 5

Population A. Group 3:

| SERUM NO. | # UNITS | TEST SCORE | REMARKS |
| --- | --- | --- | --- |
| 16 | 3.13 | positive | sick individual |
| 17 | 1.57 | reconfirmation | sick individual |
| 18 | 1.59 | reconfirmation | sick individual |
| 19 | 5.39 | positive | sick individual |
| 20 | 1.97 | reconfirmation | sick individual |
| 21 | 2.29 | positive | sick individual |
| 22 | 0.48 | negative | sick individual |

TABLE 6

Population A. Group 4:

| SERUM NO. | # UNITS | TEST SCORE | REMARKS |
| --- | --- | --- | --- |
| 23 | 1.54 | reconfirmation | normal control |
| 24 | 1.76 | reconfirmation | normal control |
| 25 | 0.58 | negative | culture negative |
| 26 | 1.03 | negative | culture negative |
| 27 | 0.79 | negative | culture negative |
| 28 | 0.89 | negative | culture negative |

TABLE 7

Population B. Non-Endemic range:
Group 1:

| SERUM NO. | # UNITS | TEST SCORE | REMARKS |
| --- | --- | --- | --- |
| 1 | 2.24 | positive | culture positive |
| 2 | 2.53 | positive | culture positive |
| 3 | 4.40 | positive | culture positive |
| 4 | 14.95 | positive | culture positive |
| 5 | 16.82 | positive | culture positive |
| 6 | 10.54 | positive | culture positive |
| 7 | 5.70 | positive | culture positive |
| 8 | 6.72 | positive | culture positive |
| 9 | 5.06 | positive | culture positive |

TABLE 8

Population B.
Group 2:

| SERUM NO. | # UNITS | TEST SCORE | REMARKS |
| --- | --- | --- | --- |
| 10 | 1.04 | negative | healthy individual |
| 11 | 0.92 | negative | healthy individual |
| 12 | 0.85 | negative | healthy individual |
| 13 | 0.20 | negative | healthy individual |
| 14 | 0.42 | negative | healthy individual |
| 15 | 0.90 | negative | healthy individual |
| 16 | 0.35 | negative | healthy individual |
| 17 | 0.73 | negative | healthy individual |

TABLE 9

Population B.
Group 3:

| SERUM NO. | # UNITS | TEST SCORE | REMARKS |
| --- | --- | --- | --- |
| 18 | 2.23 | positive | sick individual |
| 19 | 4.70 | positive | sick individual |
| 20 | 1.22 | reconfirmation | sick individual |
| 21 | 1.43 | reconfirmation | sick individual |
| 22 | 2.21 | positive | sick individual with TB history |
| 23 | 6.38 | positive | sick individual |
| 24 | 1.59 | reconfirmation | sick individual |

TABLE 10

Population B.
Group 4:

| SERUM NO. | # UNITS | TEST SCORE | REMARKS |
| --- | --- | --- | --- |
| 25 | 0.20 | negative | patient resistant to drug therapy |

We claim:

1. A method for identifying a Mycobacterial species responsible for a mycobacterial infection in human, comprising the steps of:
   a) selecting a known Mycobacterial species from the group consisting of *M. tuberculosis, M. bovis, M. avium, M. leprae,* Bacillus Calmette-Guerin, and RIVM 7114;
   b) preparing an antigenic preparation from said known Mycobacterial species comprising a mixture of at least two immuno-cross-reactive antigen components;
   c) electrophoretically separating said antigen components in the antigenic preparation and binding said antigen components to a carrier to provide a bound antigenic preparation in a standard banding pattern among said separated antigen components;

d) contacting said bound antigenic preparation with an antibody-containing sample from an individual infected with an unknown Mycobacterial species, wherein antibodies in said sample bind specifically to at least one immune cross-reactive antigen component present in said bound antigenic preparation to form antigen-antibody complexes;

e) making visible said antigen-antibody complexes; and f) identifying said unknown Mycobacterial species based on a species-identifying banding pattern of said visualized set of antigen-antibody complexes, wherein:

a banding pattern consisting of bands 10 KDa, 14 KDa, 16 KDa, 10–16KDa, 22 KDa, 22–28 KDa, 29/33 KDa, 31 KDa, 33 KDa, 33–38 KDa, 38–40 KDa, 58–60 KDa, 68 KDa, and 64/65 KDa is species-identifying for *M. tuberculosis,* a banding pattern consisting of band 10–16 KDa is species-identifying for *M. bovis,* a banding pattern consisting of bands 10–16 KDa, 58–60 KDa, and 68 KDa is species-identifying for *M. avium,* a binding pattern consisting of bands 29/33 KDa and 64/65 KDa is species-identifying for *M. leprae,* a binding pattern consisting of bands 22 KDA, 25 KDa, 27 KDa, 29/33 KDa, 31 KDa, 45/48 KDa, 64/65 KDa, and 66 KDa is species-identifying for Bacillus Calmette-Guerin, and a binding pattern consisting of bands 22 KDa, 25 KDa, 45/48 KDa, and 66 KDa is species-identifying for RIVM 7114.

2. The method of claim 1 where said carrier is a membrane to which said antigen components are bound by means of electroblotting.

3. The method of claim 2 wherein said membrane is a nitrocellulose membrane.

4. The method of claim 1 wherein said antigen preparation of said known Mycobacterial species is a total protein preparation.

5. The method of claim 4 wherein said antigen preparation is a KP-100 or SP-100 fraction of said total protein preparation.

6. The method of claim 1 wherein said carrier is a microtiter plate, said method further comprising:

in step c), placing separated antigen components into individual wells of said plate; and in step d), removing antibodies which do not bind with said antigen components.

7. The method of claim 6 wherein said antigen-antibody complexes are made visualizable using at least one antibody-enzyme conjugate directed against one or more antibodies of an isotype chosen from IgG, IgM, or IgA.

8. The method of claim 7 wherein the enzyme of said antibody-enzyme conjugate is peroxidase.

* * * * *